United States Patent [19]
Coble et al.

[11] Patent Number: 5,451,524
[45] Date of Patent: Sep. 19, 1995

[54] IN VITRO CHAMBER FOR HUMAN ORGAN TISSUE SAMPLES

[75] Inventors: Don Coble, Frederick; Kristina N. Prodouz, Bethesda, both of Md.

[73] Assignee: The Gillette Company, Boston, Mass.

[21] Appl. No.: 189,764

[22] Filed: Feb. 1, 1994

[51] Int. Cl.⁶ .............. C12M 1/00; C12M 1/06; C12M 1/18; C12M 3/00
[52] U.S. Cl. .................. 435/301; 435/284; 435/297; 435/298; 435/299; 435/300; 220/23.8; 220/420; 220/422; 220/427; 220/426; 34/192; 34/195; 34/197; 261/125; 422/205
[58] Field of Search ............ 435/284, 297–301; 220/21, 23.8, 420, 422, 427, 428, 426; 34/192, 195, 197, 199, 237, 238; 261/DIG. 3, 125; 422/99, 102, 205; 436/809

[56] References Cited
U.S. PATENT DOCUMENTS

| | | | |
|---|---|---|---|
| 3,554,704 | 1/1971 | Ushakoff | 436/809 |
| 4,090,921 | 5/1978 | Sawamura et al. | 195/127 |
| 4,195,131 | 3/1980 | Papas | 435/291 |
| 4,657,867 | 4/1987 | Guhl et al. | 435/284 |
| 4,673,651 | 6/1987 | Rothenberg et al. | 435/301 |
| 4,707,086 | 11/1987 | Dahan et al. | 350/536 |
| 4,786,601 | 11/1988 | Rothenberg | 435/301 |
| 4,822,741 | 4/1989 | Banes | 435/300 |
| 4,940,853 | 7/1990 | Vandenburgh | 435/240.23 |
| 4,974,952 | 12/1990 | Focht | 350/536 |
| 5,153,136 | 10/1992 | Vandenburgh | 435/284 |
| 5,238,140 | 8/1993 | Maze | 220/506 |
| 5,366,893 | 11/1994 | Stevens et al. | |

OTHER PUBLICATIONS
Fisher Catalog pp. 1534, 1538, 1539, 1546 Fisher Scientific, 1992.

*Primary Examiner*—Michael G. Wityshyn
*Assistant Examiner*—Jane Williams
*Attorney, Agent, or Firm*—Stephan P. Williams

[57] ABSTRACT

An in vitro chamber for sustaining organ tissue samples during optical study with, for example a microscope, has a tray assembly with a plurality of wells, each of which may be provided with a clampable sleeve or a vertically adjustable thimble such that an associated organ tissue sample contacts a nutrient medium contained in a reservoir. The tray assembly rests upon a heater assembly having a water-jet-driven magnetic stirrer magnetically coupled with a driven magnetic stirrer in the nutrient reservoir to maintain a substantially uniform temperature in both the heater assembly and the nutrient reservoir. A thermally insulating collar surrounding the tray assembly and the heater assembly maintains relative positions thereof. A transparent cover encloses the top of the tray assembly so that air borne exchanges with the wells and nutrient splashes are substantially contained.

7 Claims, 5 Drawing Sheets

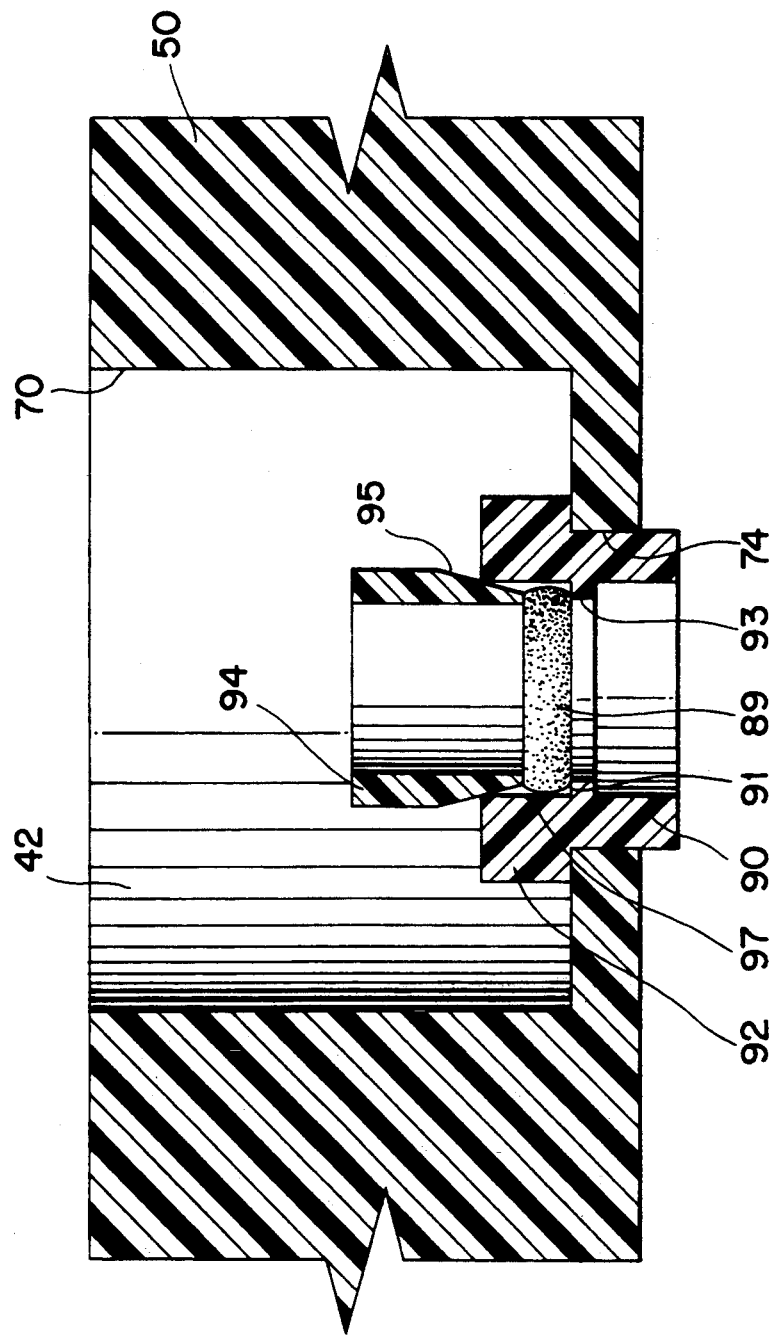

IN VITRO CHAMBER FOR HUMAN ORGAN TISSUE SAMPLES

BACKGROUND OF THE INVENTION

The present invention relates generally to an in vitro chamber for sustaining human tissue samples during study. More particularly, this invention concerns a portable in vitro chamber adapted for use with a microscope while maintaining viability of human organ tissue samples for at least one day.

For purposes of this invention, the terms "organ tissue samples" and "tissue cultures" are to be distinguished from one another. As used herein, an "organ tissue sample" is a multicellular system such as might be obtained from a tissue biopsy or a skin specimen and includes hair, fingernails, sweat glands, and sebaceous glands. By contrast, "tissue culture" refers to a single cell type which may be nurtured for growth studies, and typically requires a substrate on which the cells grow.

Generally speaking, the concept of an in vitro chamber merely for sustaining human tissue cultures is not unique. In vitro propagation of cells conventionally occurs in culture plates or bottles manufactured from polystyrene or glass. To culture cells, the cells may be inoculated into flasks, single culture dishes or multi-well plates. A nutrient medium is added and the cells are incubated under controlled conditions. Alternatively, cells can be grown in continuously rolling bottles, on glass or polysaccharide beads, on tissue segments, or suspended in a suitable culture medium. Other methods also exist in which deforming stresses are applied to the cells to simulate cyclic stresses encountered for example in heart and lung cells.

For example, it is known in the prior art to use an apparatus having a plurality of individual wells, each having a movable membrane as the bottom wall thereof and each having a tissue culture therein. The upper surface of the membrane may be coated with an extra-cellular material, such as rat tail collagen, to adapt the membrane to permit attachment of tissue cells. A suitable clear plastic cover may be provided for the wells. Mechanical stretching of the membranes in each well stimulates the tissue culture. Suitable nutrients can be supplied to the tissue cultures contained in the various wells. Apparatus of this type is described more fully in U.S. Pat. No. 4,940,853 issued to Vandenburgh on Jul. 10, 1990, and U.S. Pat. No, 5,153,136 issued to Vandenburgh on Oct. 6, 1992. The present invention, however, is principally concerned with non-cyclically stressed organ tissue samples.

Other multiwell tissue culture assemblies are also known. For example, it is known to provide a plate having a multiplicity of frustoconical wells therein, each well adapted to receive a liquid cell culture medium for cell cultures. A specially designed cover may cooperate with the well plate to minimize airflow between the wells and the external environment so as to minimize evaporation, while permitting such an airflow exchange to exist thereby maintaining equilibration. U.S. Pat. No. 4,657,867 issued to Guhl et al. on Apr. 14, 1987, is an example of such an apparatus.

Multiwell apparatus have also been proposed which overcome the "edge effect" associated with some tissue culture holders by specially designing a base and cover arrangement from a suitable transparent plastic material. The base includes a plurality of tissue culture wells. A peripheral baffle around the base extends above the culture wells and is enclosed by the cover arrangement Gas may be distributed above the culture wells. To reduce uneven evaporation in the wells from air circulating around the assembly, the bottom of the base includes an insulating chamber. That insulating chamber may be filled with a clear liquid that may be either heated or cooled while permitting observation of the tissue wells by a conventional inverted microscope. Examples of these devices can be found in the Rothenberg et al. U.S. Pat. Nos. 4,673,651 issued Jun. 16, 1987, and 4,786,601 issued Nov. 22, 1988.

Various materials are also known for use in in vitro cell culture studies. As a specific example, surface-modified polyorganosiloxane compositions are known which demonstrate improved biocompatibility in cell culture apparatuses. See for example, U.S. Pat. No. 4,822,741, issued to Banes on Apr. 18, 1989.

Moreover, it is known to provide specially adapted microscope stages for optical examination of tissue culture studies. One such microscope stage having a single chamber arranged for circulation of a fluid under thermally controlled conditions. See for example U.S. Pat. No. 4,974,952 issued to Focht on Dec. 4, 1990. Another single chamber device for microscope stages also has a cylindrical chamber but provides for fluid flow through the chamber as well as thermally controlled fluid adjacent to the chamber. This device also appears to be adapted for tissue culture studies through its several references to petri dishes. See for example U.S. Pat. No. 4,195,131 issued to Papas on Mar. 25, 1980.

Automatic cultivating apparatus for tissue cultures in combination with an optical inspection assembly having a light source and various lenses is also known. Tissue culture wells are carried by an annular disk into successive registry with the optical inspection assembly. The atmosphere within the apparatus is controlled. See for example U.S. Pat. No. 4,090,921 issued Sawamura et al. on May 23, 1978.

In other technologies, microscope state assemblies have also been designed to accommodate variant temperature and pressure ranges in a single chamber sealed envelope with optical windows. See for example U.S. Pat. No. 4,707,086 issued to Dahan et al. on Nov. 17, 1987.

One device is known for maintaining single organ tissue sample where the sample rests on a concave plate with a central opening. The concave plate, in turn, is supported above a peripherally heated reservoir containing a suitable medium, a gas probe, a temperature monitor, and a magnetic stirring device. That device, however, was cumbersome, had so much peripheral matter that it could not be used on a microscope, and created a potential health hazard when operating due to splashing of medium, and exposure of the medium when the concave plate was removed.

Despite the existence of a device for maintaining in vitro a single organ tissue sample, there continues to be a need for devices which can be operatively connected with a conventional stereo microscope for examination and study. Known devices cannot be so used since associated heater assemblies interfere with placement of the container on a microscope stage. In a similar vein, complicated studies of human organ tissue require that multiple specimens be simultaneously observed and examined over periods of time. Furthermore, considering the heightened concern of exposure to HIV viruses when working with human tissue samples, there is a need to contain both the tissue samples and all fluids coming into contact with them. Recognizing that it can be desirable to begin in vitro support for organ tissue samples immediately following removal from the host body, there is also a need for a portable chamber.

Thus, a need continues to exist for an in vitro chamber adapted for use in microscope studies of human organ tissue.

BRIEF SUMMARY OF THE INVENTION

An in vitro organ tissue chamber which overcomes problems of the type discussed above and provides the desirable attributes mentioned includes a tray assembly for holding in vitro organ tissue samples. The tray assembly includes a top, a bottom, and a plurality of wells each of which is adapted to hold an organ tissue sample, and a reservoir assembly adjacent to the bottom for holding nutrient solution. A transparent cover for the container is positioned on the top of the tray assembly and operates in conjunction with the tray assembly to contain gases above the tray assembly as well as to contain fluid splashes from the reservoir means and the wells. The container further includes a heater assembly having a top surface for supporting the tray means in heat transfer relationship and a planar bottom surface for substantially unimpeded placement on a microscope stage. The heater assembly is operable to provide a substantially constant temperature heat source for the nutrient reservoir.

To maintain the relative position of the tray assembly and the heater assembly, a peripheral collar may be provided. Ordinarily, a ledge is defined between the bottom surface of the tray assembly and the top surface of the heater assembly due to different sizes of the juxtaposed surfaces. The collar extends above and below the interface between the juxtaposed surfaces and includes a land in abutment with the ledge. The collar receives at least a portion of the perimeter wall of the heater assembly and at least a portion of the perimeter wall of the tray assembly. The collar also extends above the interface so that the nutrient reservoir is completely surrounded thereby. In this manner, by fabricating the collar from an insulating material, heat losses from the nutrient reservoir are further minimized.

The heater assembly includes an inlet port and an outlet port in its peripheral wall, and a tank communicating with those ports for receiving a circulating temperature-conditioned fluid, such as water. To maintain a uniform temperature throughout both the tank and the medium reservoir, a stirring arrangement is provided. In a preferred embodiment, a magnetic driving element is rotatably mounted on a generally vertical axle in the heater assembly. The magnetic driving element is encased in a low friction material and is driven by water flowing through the heater assembly. A magnetically coupled stirring element is positioned in the nutrient reservoir and rotates in unison with the magnetic driving element. Accordingly, the driving element circulates water in the tank so that its temperature is substantially uniform at the same time that the stirring element circulates medium in the reservoir to maintain a substantially uniform temperature therein while maintaining a substantially homogeneous concentration of nutrients throughout.

The tray assembly may include a well plate attached to a reservoir housing with a fluid seal therebetween to thereby facilitate periodic cleaning of the reservoir. Each well of the well plate communicates with the reservoir so that access to a common nutrient supply is provided for each well. The wells may be provided with one of two different tissue holding arrangements. In one arrangement, the well has an opening in the bottom and an annular gasket is positioned at that bottom. A tissue thimble is frictionally positioned by the gasket relative to the well, so that the bottom of the thimble is in fluid communication with the nutrient reservoir. By virtue of the frictional engagement with the gasket, the tissue thimble can be vertically adjusted.

Another arrangement for suspending tissue samples involves inclusion of a flanged sleeve in the opening in the bottom of a well. Cooperating with the flanged sleeve is a cylinder clamp having a tapered end portion. Part of the tapered end portion is received the upper portion of the generally cylindrical sleeve. The sleeve and the cylinder clamp cooperate to peripherally clamp, and support or suspend a tissue sample so that the tissue sample contacts the nutrient medium of the reservoir assembly.

The well plate may also include a plurality of wells arranged in a radial pattern to facilitate common observation by a microscope.

BRIEF DESCRIPTION OF THE DRAWINGS

Many additional objects and advantages of the present invention will be apparent to those skilled in the an when this specification is read in conjunction with the attached drawings wherein like reference numerals have been applied to like elements and wherein:

FIG. 5 is a detail view of one of the organ tissue support devices.

DETAILED DESCRIPTION OF THE PREFERRED EMBODIMENT

Figure 1:
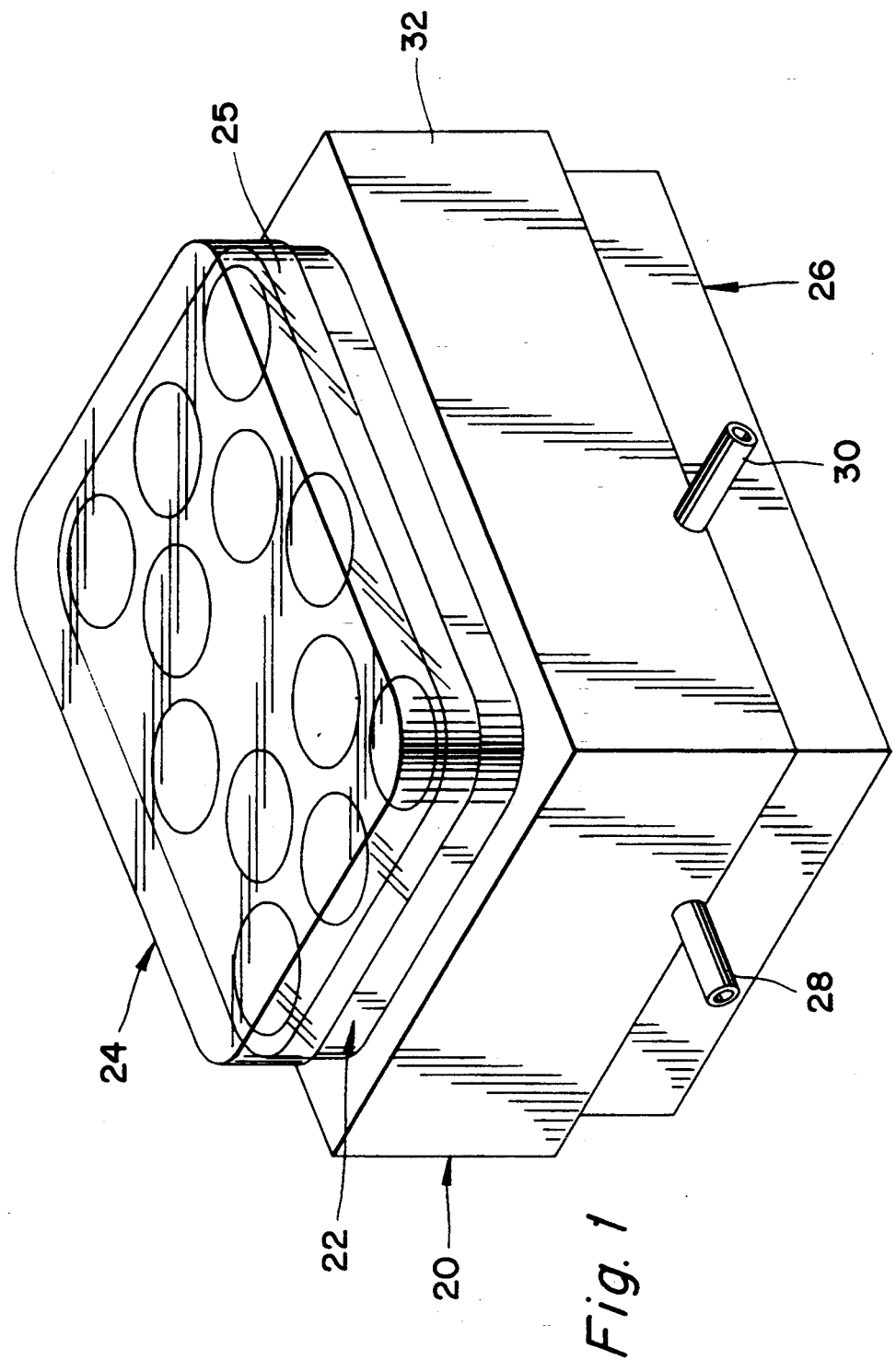
FIG. 1 is a perspective view of an in vitro chamber for human organ tissue according to this invention.

An in vitro chamber 20 (see FIG. 1) suitable for overcoming problems of the type discussed above includes a tray assembly 22 having a plurality of wells, each of which is capable of receiving and holding an organ tissue sample. The organ tissue samples may be biopsy specimens, or other live tissue specimens selected for interest in any of a variety of studies. A transparent cover 24 rests on top of the tray assembly 22 and permits visual and optical inspection of the various wells. The cover 24 includes a skirt 25 which extends downwardly from the cover so as to peripherally surround the tray assembly 22. In this way, the skirt retains the cover 24 from sliding off the tray assembly 22.

In addition, the transparent cover 24 cooperates with the tray assembly 22 to define a contained gas volume above the wells. That contained gas volume restrains contaminants in ambient air from reaching the organ tissue samples being maintained. Furthermore, the contained gas volume restrains escape of viruses and microbes from the chamber when diseased organ tissue specimens are being studied. A final aspect of the contained gas volume is that the cover 24 may be further provided with a gas inlet port and a gas exhaust port. By connecting the gas inlet port and the gas outlet port to a suitable conventional gas circulating and temperature control system, the contained gas volume may be used to flood the container with any desired gas under selected temperature conditions.

The tray assembly 22 rests upon and is supported in heat transfer relationship by a heater assembly 26. Preferably, the heater assembly 26 contains a tank through which a suitable, conventional heat transfer fluid circulates. One of the most readily available, and most inexpensive heat transfer fluids is water. In order that the heat transfer fluid may circulated into and out of the heater assembly 26, an inlet conduit 28 and an outlet conduit 30 pass through a peripheral wall of the heater assembly 26 for connection with tubes, or hoses, associated with the water supply. Normally, the water supply will include a conventional pump (not shown) and temperature control means (not shown) for supplying water to the heater assembly 26 at a pre-selected temperature.

To hold the tray assembly 22 in lateral position with respect to the heater assembly 26 and to provide enhanced thermal insulation around the tray assembly 22, a collar 32 surrounds the lower portion of the tray assembly 22 and the upper portion of the heater assembly 26. An internal surface of the collar 32 is proportioned to closely conform to the external contour of the tray assembly 22 as well as the external contour of the heater assembly 26.

Figure 2:
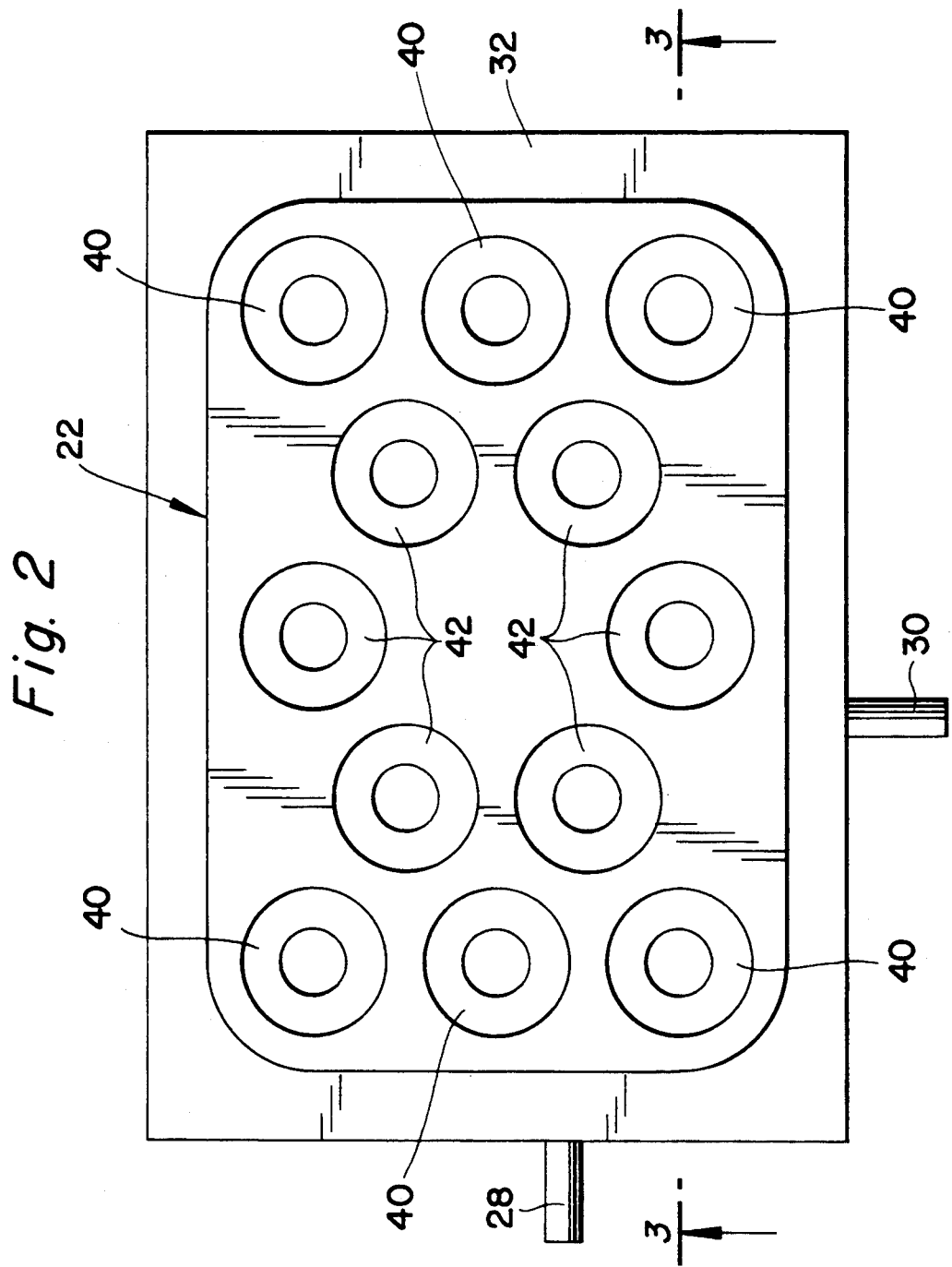
FIG. 2 is a plan view of the in vitro chamber of FIG. 1 but with sample holding arrangement removed.

Now, the tray assembly 22 includes a plurality of wells as previously noted. Various arrangements of the wells are possible depending upon the needs of the experiment, and the requirement of the optical inspection equipment. For example, a tray assembly 22 having twelve wells might arrange those wells in four rows of three wells each. Alternatively, the wells might be arranged as shown in FIG. 2. More particularly, six wells 40 may be arranged in two rows of three each, each row being positioned near a corresponding side of the tray assembly 22. The remaining six wells 42 might be arranged in a circle which is itself centered on the top surface of the tray assembly 22. Where the container will be monitored from above by a suitable conventional video camera assembly or by a conventional stereo microscope, the circular arrangement of the central wells 42 allows organ tissue specimens to be located at approximately the same location on the lens so that organ tissue specimens in the central wells 42 should have a common focus.

It will also be noted that the tray assembly 22 is symmetric about a longitudinal vertical plane, but asymmetric about a perpendicular plane. With such a configuration, identification of the individual wells 40, 42 for record-keeping purposes may be facilitated.

Figure 3:
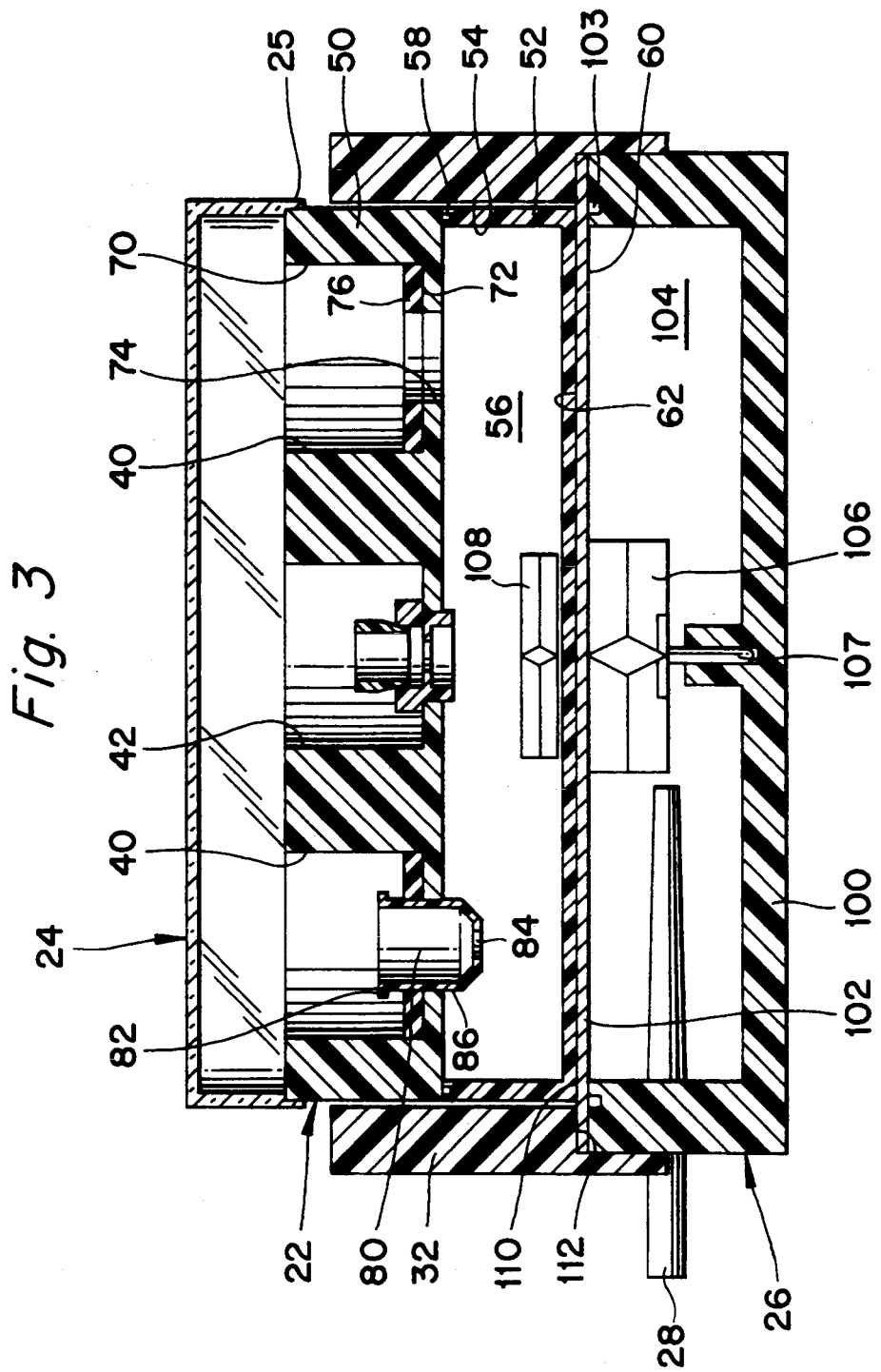
FIG. 3 is a cross sectional view of the in vitro chamber taken along the line 3—3 of FIG. 2.

Further details of the in vitro chamber are best understood by reference to FIG. 3. More particularly, the tray assembly 22 includes a well plate 50 which is mounted on and secured to a reservoir chamber 52. Both the well plate 50 and the reservoir chamber 52 may be fabricated from a methyl methacrylate-type polymer, such as Plexiglas. Generally, the well plate 50 is provided with a substantial thickness so that the thermal insulation properties of the material can be advantageously used to restrict heat loss from the top of the reservoir chamber 52. In addition, the well plate 50 and the reservoir chamber 52 are intentionally made in two separate pieces. It has been found that it is necessary to clean the reservoir chamber 52 after extended periods of use. Constructing the chamber 52 so that the well plate 50 can be removed for cleaning permits much easier cleaning of the chamber.

The reservoir chamber 52 and the well plate 50 have substantially identical contours when viewed from above so that both the well plate 50 and the reservoir chamber 52 can be received in the upper section 54 of the collar 32. The reservoir chamber 52 has a substantially uniform wall thickness and defines an interior reservoir 56 for holding organ-tissue-nutrient fluid. To prevent fluid leakage from the joint between the well plate 50 and the reservoir chamber 52, a suitable conventional seal 58 is provided in a peripheral groove that extends completely around the perimeter of the top face of the reservoir chamber 52. That top face also abuts the bottom surface of the well plate 50. The bottom surface 60 of the reservoir chamber 52 is preferably planar since it is in direct contact with and in heat transfer relationship with, the upper planar surface 62 of the heater assembly 26. Because of that heat transfer relationship, the bottom of the reservoir chamber 52 is made as thin as practical.

Turning now to details of the wells themselves, each well 40, 42 is defined in part by a counterbore 70 which does not extend all the way through the thickness of the well plate 50. Thus, the counterbore 70 defines an annular seat 72. A central opening 74 provides communication with the reservoir 56 disposed beneath the well plate 50. The central openings of the various wells may be the same diameter, or different diameters, as desired.

Each well 40 is provided with an annular gasket 76 having a central opening with a diameter that is at least slightly less than the diameter of the central opening 74 of the corresponding well 40. The wells 40 are each adapted to receive an organ-tissue holding thimble 80. The thimble 80 includes a flange 82 that extends radially outwardly at the top edge surface. By establishing the radial extent of the flange so that it exceeds the diameter of the opening through the gasket 76, the thimble is prevented from passing completely through the well plate 52 by interference between the flange 82 and the gasket 76.

Moreover, the thimble 80 has a substantially closed end provided with a small diameter opening 84 so that fluid communication can be established with the reservoir 56. Further, the thimble 80 preferably has a generally cylindrical side wall 86 which is frictionally engaged by the inner surface of the gasket 76 opening. By virtue of that frictional engagement, the thimble 80 can be vertically adjusted relative to the well plate 50, within the associated cell 40. Thus, the level of nutrient fluid above the thimble end can be independently controlled for each thimble 80.

An alternative arrangement for holding organ tissue specimens is seen in well 42 (see enlarged view in FIG. 5). There a sleeve 90 is positioned in the opening 74 of the well. The sleeve 90 has a cylindrical portion which extends downwardly through the opening 74 and a radially outwardly extending flange 92 at the upper edge surface thereof. The sleeve 90 has a centrally open channel 97 therethrough with an organ-tissue support surface 91 that extends across that channel. The support surface 91 includes a central opening 92 sized as desired to establish fluid communication between the bottom surface of an organ tissue specimen 89 and the reservoir 56. Normally, the opening 93 will be as large as possible such that a radially inwardly extending land remains to peripherally support the organ tissue specimen 89. That opening 93 may, for example, be about of the specimen diameter. When it is desired to clamp the peripheral edge of an organ tissue specimen 89, an annular clamp 94 may be used with the sleeve 90. The clamp 94 preferably has an external diameter that exceeds the diameter of the channel 97 and a frustoconically tapered end 95 where the diameter of the clamp varies from a value larger than the channel diameter to a value smaller than the channel diameter. Preferably the height of the flange 92 is about twice the thickness of typical organ tissue specimens to be maintained and studied. Furthermore, the tapered end 95 is preferably designed so that it will extend into the central opening 97 by a distance corresponding to the typical thickness of an organ tissue specimen. As a result, the clamp 94 will peripherally engage and hold the organ tissue specimen in the sleeve 90.

Where pieces of a sample of organ tissue are to be examined and studied, the actual specimens may be punched from the larger sample-resulting in disk shaped specimens. Such disk shaped specimens are well adapted to being held in the clamping-type sample holder of FIG. 5.

The thimble 80 arrangement (FIG. 3) provides a tissue supporting arrangement which is well adapted for specimens that must be supported from below but do not need peripheral clamping. But, for specimens that need support from the side, the sleeve 90 provides a preferred arrangement. Naturally, there are other specimen support arrangements which can be used in combination with the tray assembly of this invention.

At the bottom of the assembly, the heater arrangement 26 includes a tank defined in part by a generally rectangular tray 100 having a cover 102 attached thereto with a peripheral seal 103 therebetween to prevent leakage. The tray 100 and the cover 102 cooperate to define a tank 104 containing the heater liquid. The tray 100 may be fashioned from a suitable structural plastic such as polyvinyl chloride (PVC) to take advantage of its thermal insulation properties. To this end, the peripheral walls and the bottom of the tray 100 are designed to be comparatively thick to take advantage of the thermal insulating properties. On the other hand, the cover 102 is preferably fashioned from a metal such as stainless steel to take advantage of its thermal conductivity properties. The cover 102, and the bottom of the reservoir plate 52 have relatively thin wall thickness in comparison to the walls of the tank 104. These thinner walls enhance heat transfer from the heater assembly 26 to the reservoir 56.

A mixing device 106 is located within the tank 104 and operates in conjunction with a mixing device 108 located in the reservoir 56. It has been found that a magnetically coupled mixing devices are particularly well adapted for use with this chamber. The mixing device 106 is operable to agitate fluid in the tank 104 thereby promoting turbulence and thermal mixing of the fluid in that tank. Similarly, the driven mixing device 108 is operable to agitate fluid in the reservoir 56 thereby promoting turbulence and thermal mixing of the fluid therein.

Figure 4:
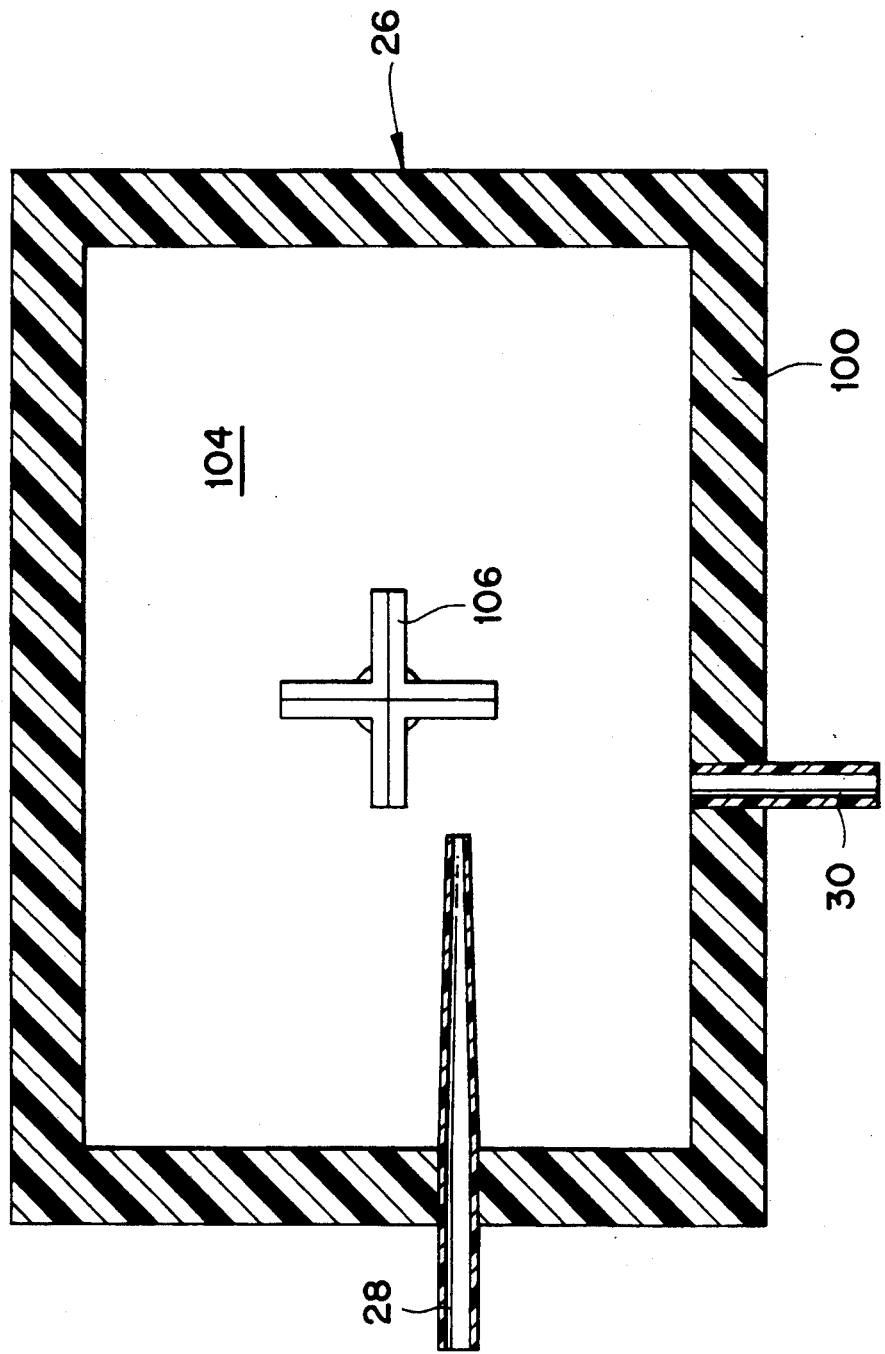
FIG. 4 is a plan view of the heater assembly with the top removed to show the turbine-driven magnetic stirring device.

The driving mixing device 106 is fixed to a shaft 107 which is rotatably received in a corresponding bore provided in a boss protruding upwardly from the bottom of the tray 100. The mixing device 106 may, for example, have a cross-like shape when viewed from above (see FIG. 4). Each arm of the mixing device 106 may contain a suitable bar magnet. In addition, the device 106 is preferably fashioned from a low friction material such as tetrafluoroethylene (Teflon). The arms may have a rhombic cross-sectional shape as seen in FIG. 3. The top of the device 106 has a very small vertical clearance from the top plate 102 of the tank 100. Thus, the top plate 102 functions as a bearing surface against which the low friction material of the device 106 rubs. That arrangement prevents wobbling of the device 106 as it rotates.

The driven device 108 may be constructed with a similar cross-shape and with a similar rhombic cross section. If desired, the driven device 108 may be smaller than the driving device 106. In addition, by encasing magnets of the driven device 108 in tetrafluoroethylene (such as Teflon), friction between the driven device 108 and the bottom of the reservoir is reduced. The driven device 108 is not mounted on any bearings and is not physically constrained to a particular location in the reservoir other than through magnetic coupling with the driving device 106.

Water introduced through the inlet tube 28 is used to drive the device 106. More particularly, the inlet tube 28 is positioned to one side of the axis of rotation for the device 106 (FIG. 4) at an elevation in alignment with the device 106. Moreover, the inlet tube 28 has a tapering cross-sectional area which terminates with a small area creating a higher velocity water jet. The water jet causes the device 106 to rotate. As the driving device rotates, the magnetically coupled, driven device 108 also rotates.

It will also be noticed that the top 62 of the cover 102 is not coextensive with the bottom 60 of the tray assembly 22. The difference between the planar extent of these two surfaces defines a ledge 110 which extends around the perimeter of the superposed tray assembly 22 and heater assembly 26. Preferably, as illustrated, the ledge 110 faces upwardly and thus supports the collar 32. Regardless of the orientation of the ledge 110, the collar 32 has an internal land 112 designed to abut the ledge 100. By fabricating the collar 32 from an insulating material such as PVC heat transfer from the heating means 26 is principally directed to the reservoir 56. With the ledge 110 supporting the collar 32, the tray assembly 22 is prevented from sliding relative to the heating means 26. Moreover, when the heating means 26 is moved, the entire container moves simultaneously.

It will be further noted that the shape of the wells 40, 42 need not be circularly cylindrical as illustrated. Other shapes such as square or polygonal cylinder can be used. The circularly symmetrical wells are preferred, however, due to their ease of manufacture.

In the same vein, the peripheral shape of the tray assembly and the heater assembly are not deemed to be critical. It is of course important that part of the peripheral surfaces be received by the collar for lateral stability.

One or more of the wells may be used for access to the reservoir 56 so that the reservoir can be supplied with gas and so that the reservoir temperature can be monitored. Typically, 5% $CO_2$ with $O_2$ are bubbled in the reservoir medium which may be a basic buffered salt solution having physiologic concentrations of ions and electrolytes.

In use, a plurality of organ tissue specimens is loaded into the tray assembly, one organ tissue specimen being placed in a corresponding well. Where the organ tissue specimen must be supported from below, it is placed in a thimble 80. Where the specimen can be peripherally supported, it is located in a cell with a sleeve. Liquid tissue nutrient solution (i.e., the basic buffered salt solution) is charged in the reservoir 56. Normally, the nutrient will completely fill the reservoir 56. Accordingly, the nutrient solution will enter the thimble supports and reach into the central cavity of the sleeve arrangements to contact the bottom surface of the organ tissue specimens.

Temperature controlled water is supplied to the heater means 26. As water passes through the reduced area at the end of the inlet 28, it forms a water jet that impinges upon the driven magnetic stirring element 106, causing it to rotate about its axis. As the element 106 rotates, the magnetically coupled element 108 also rotates. Thus, the circulating water causes mixing in both the heater 26 and the reservoir 56. Since the volume of the tank 104 substantially exceeds the water flow rate through the tank, actuation of the magnetic stirrer 106 establishes a well mixed and uniform temperature throughout the heater means 26. With the high thermal conductivity lid of the heater 26 in surface-to-surface contact with the thin bottom of the reservoir, heat is readily transferred from the top of the heater assembly 26 to the bottom of the tray assembly 22 and into the reservoir 56, so that the nutrient medium is maintained as a substantially constant temperature.

To the extent it may be desired, with the cover 24 in place, a preferred gas can flow through or wash the containment space.

Having a completely flat bottom surface on the heater assembly 26 which is free of obstructions and attachments, the container of the present invention can be bodily positioned on the stage of a conventional stereo microscope for observation of organ tissue samples in individual wells. As it becomes necessary, the entire container is moved on the microscope stage to place particular wells in registry with the optical path of the microscope.

Alternatively, if the organ tissue samples are to be monitored by a television or video camera, the container is positioned with the lens centered on the top of the tray assembly. As a result of the arrangement of the wells, the video camera will be focused on the majority of tissue samples simultaneously.

With the present invention, it is possible to study a plurality of organ tissue samples over time and record the results with a video camera. Moreover, the top surfaces of the various organ tissue samples can be subjected to various liquid neuro-receptor agonists and antagonists in different wells so that their respective effects can be evaluated. In addition, the space between the well plate and the cover can be bathed with desired gases to assess the further effect of such gases.

As the container is moved from place to place, or as the container is moved about on the microscope stage, any nutrient that splashes from the wells will be contained by the cover. Likewise, any viral or microbial materials which may be found in the specimens will be contained by the presence of the cover and restrained from escape to the environment.

It will now be apparent to those skilled in the art that a new in vitro chamber for sustaining organ tissue samples has been shown and described which overcomes problems of the type associated with previous devices. Moreover, it will also be apparent that there are numerous modifications, variations, substitutions and equivalents for features of the invention which do not materially depart from the spirit and scope of the invention described herein. Accordingly, it is expressly intended that this invention shall encompass all such modifications, variations, substitutions, and equivalents which fall within the spirit and scope of the inventions as defined by the appended claims.

What is claimed is:

1. A chamber for sustaining tissue samples in vitro for optical microscopic examination comprising:
   a tray assembly including a top portion and a bottom portion, the bottom portion comprising a reservoir chamber for holding nutrient solution, the top portion comprising a well plate having a plurality of wells, each of the wells being adapted to hold a tissue sample and having an opening through the bottom of the well plate, the top portion being removably, but sealingly, mounted to the bottom portion such that the wells are in communication with the reservoir chamber in a manner that allows tissue samples placed in the wells to be contacted by nutrient solution placed in the reservoir chamber;
   a transparent cover positioned over the top portion of the tray assembly and operable in conjunction therewith to contain gases above the wells and prevent contaminants from passing into or out of the wells;
   a heater assembly having a top surface with a high heat transfer capacity for supporting the tray assembly in heat transfer relationship therewith and a planar bottom surface for substantially unimpeded placement on a microscope stage, the heater assembly including a tank for containing a temperature regulating fluid, the tank having an inlet conduit and an outlet conduit for circulating the temperature regulating fluid.

2. The chamber of claim 1 further including first stirrer means within the reservoir chamber to mix nutrient solution placed therein and second stirrer means within the tank to mix temperature regulating fluid placed therein, wherein the first and second stirrer means are magnetically coupled such that rotation of one stirrer means causes rotation of the other stirrer means.

3. The chamber of claim 2 wherein the inlet conduit and the second stirrer means are positioned such that fluid entering the tank through the inlet conduit causes the second stirrer means to rotate.

4. The chamber of claim 3 further including an insulating collar tightly surrounding a lower portion of the tray assembly and an upper portion of the heater assembly so as to prevent lateral movement therof and provide thermal insulation.

5. The chamber of claim 4 wherein at least one well includes an annular gasket with a central opening and a tissue holding thimble frictionally engaged within the central opening of the annular gasket such that the tissue holding thimble may be vertically adjustably positioned therewithin for communication with nutrient solution.

6. The chamber of claim 4 wherein at least one well includes a cylindrical sleeve with an annular tissue support surface therewithin and a frustoconically tapered annular clamp frictionally engaged within the sleeve to hold a tissue sample placed on the tissue support surface.

7. The chamber of claim 4 wherein the wells are arranged in a radial pattern.

* * * * *